United States Patent
Ström

(10) Patent No.: US 7,121,277 B2
(45) Date of Patent: Oct. 17, 2006

(54) VENTILATOR

(75) Inventor: Christer Ström, Pitea (SE)

(73) Assignee: Maquet Critical Care AB, (SE)

( * ) Notice: Subject to any disclaimer, the term of this patent is extended or adjusted under 35 U.S.C. 154(b) by 895 days.

(21) Appl. No.: 09/922,504

(22) Filed: Aug. 3, 2001

(65) Prior Publication Data

US 2002/0082512 A1    Jun. 27, 2002

(30) Foreign Application Priority Data

Aug. 8, 2000    (SE)    ................................... 0002849

(51) Int. Cl.
*A61M 16/00*    (2006.01)
*A62B 7/00*    (2006.01)

(52) U.S. Cl. .............................. 128/204.18; 128/204.21

(58) Field of Classification Search ........... 128/204.18, 128/205.11, 205.24
See application file for complete search history.

(56) References Cited

U.S. PATENT DOCUMENTS

| | | | |
|---|---|---|---|
| 4,592,349 A * | 6/1986 | Bird | 128/204.25 |
| 4,821,709 A | 4/1989 | Jensen | |
| 4,838,257 A | 6/1989 | Hatch | |
| 5,165,398 A * | 11/1992 | Bird | 128/204.25 |
| 5,611,335 A | 3/1997 | Makhoul et al. | |
| 5,862,802 A * | 1/1999 | Bird | 128/204.18 |
| 5,871,008 A * | 2/1999 | Poon et al. | 128/202.12 |
| 5,937,853 A * | 8/1999 | Strom | 128/204.23 |
| 6,435,182 B1 * | 8/2002 | Lutchen et al. | 128/204.21 |
| 6,510,851 B1 * | 1/2003 | Rydin et al. | 128/204.21 |
| 6,533,730 B1 * | 3/2003 | Strom | 600/533 |
| 6,564,798 B1 * | 5/2003 | Jalde | 128/205.24 |

FOREIGN PATENT DOCUMENTS

| | | |
|---|---|---|
| EP | 0 548 624 | 6/1993 |
| EP | 0 671 180 | 9/1995 |
| EP | 0 776 672 | 4/1997 |
| EP | 0 965 357 | 12/1999 |
| WO | WO 00/56385 | 9/2000 |

* cited by examiner

*Primary Examiner*—Michael J. Hayes
*Assistant Examiner*—Michael Mendoza
(74) *Attorney, Agent, or Firm*—Schiff Hardin LLP

(57) ABSTRACT

A ventilator has an inspiratory unit and an expiratory valve for regulating a flow of breathing gas and a control unit for controlling the inspiratory unit and the expiratory valve. In order to facilitate the opening of collapsed alveoli in the lungs, the control unit controls the inspiratory unit and the expiratory valve to generate a recruitment phase with an elevated basic pressure for the flow of breathing gas upon which a number of breaths is superimposed at a faster breathing rate.

7 Claims, 1 Drawing Sheet

VENTILATOR

BACKGROUND OF THE INVENTION

1. Field of the Invention

The present invention relates to a ventilator of the type having an inspiratory unit and an expiratory valve for regulating a flow of breathing gas, and a control unit for controlling the inspiratory unit and the expiratory valve.

2. Description of the Prior Art

Mechanical ventilation is employed to control or support a patient's breathing. Breathing gas at a positive pressure is supplied to the patient. In many instances, ventilation is a vital necessity for the patient, however, the treatment in itself is not without risks. Numerous studies of animals suggest that ventilation can initiate or aggravate lung damage. A major contributory reason for this is the mechanical stress to which the pulmonary system may be subjected during ventilation. In particular, damage can develop or be aggravated when alveoli in the lungs cyclically open and collapse during inspiration and expiration.

Moreover, some patients suffer from such severe conditions that using a treatment that can cause some damage to the lungs is the only way to save the patient's life.

One way to prevent alveolar collapse is to impose a positive pressure on the lungs, even during expiration, with a positive end-expiratory pressure (PEEP). However, PEEP cannot be set too high, since a high PEEP can subject the lungs to harmfully high pressure during inspiration. An excessive inspiratory pressure can impede blood perfusion in the lungs (causing poorer oxygenation of the blood) and even inflicting damage to pulmonary tissue.

Recruitment phases can be employed instead of a constantly high PEEP. During a recruitment phase, the pulmonary alveoli are opened with a pressure (usually higher than the normal inspiratory pressure for the patient), enabling them to remain open when exposed to a lower pressure during a subsequent period of treatment. The recruitment phase is repeated as needed.

A number of procedures are known for instituting the recruitment phase. One is often referred to as the 40/40 method. This means that the lung is subjected to a pressure of about 40 $cmH_2O$ for up to 40 seconds.

This is a static procedure and rather hard on the lung and the patient, but it is a simple maneuver producing clear results in the form of improved oxygenation of the blood.

Another procedure involves the use of a number of brief pressure pulses, e.g. three, each lasting 15 seconds.

In principle, the effect is the same as in the aforementioned instance. However, static methods have a major shortcoming in the buildup of carbon dioxide in the lungs during the recruitment phase.

A third known procedure involves a successive increase in pressure in the lungs during, in principle, normal breaths until a satisfactory degree of opening is achieved.

This is without doubt the easiest method on the lung and patient, but it is highly demanding and difficult for staff to implement.

SUMMARY OF THE INVENTION

An object of the invention is to provide a ventilator with which at least some of the aforementioned problems can partially be avoided.

The above object is achieved in accordance with the principles of the present invention in a ventilator having an inspiratory unit and an expiratory valve for regulating a flow of breathing gas, and a control unit for controlling the inspiratory unit and the expiratory valve, wherein the control unit controls the inspiratory unit and the expiratory valve to generate a recruitment phase with an elevated basic pressure for the breathing gas, upon which a number of breaths is superimposed at a faster breathing rate.

A number of advantages are achieved with a recruitment phase consisting of a static increase in pressure combined with a superimposed series of breaths at a faster rate.

Carrying out the maneuver then becomes relatively simple whenever necessary. The maneuver is also effective, since the static pressure, combined with the superimposed breaths, leads to more effective opening of the alveoli and improved scavenging of carbon dioxide.

The magnitude of the elevated basic pressure depends on the patient and the illness, but the pressure is usually in the 10–80 $cmH_2O$ range for most patients. Preferably, a range of 30–60 $cmH_2O$ is used.

The superimposed breaths can be pressure-regulated and then have a pressure amplitude ranging from 1–10 $cmH_2O$.

Alternatively, the superimposed breaths can be volume-controlled and then have a tidal volume ranging from 1–100 ml.

The increased respiratory rate can suitably range from 50–200 breaths/minute.

The increased respiratory rate can also be viewed as a percentage of a set respiratory rate, for instance between 110% and 1000% of the rate (i.e. 10% to 100% higher than the rate). Higher percentages can be possible, depending on the set rate, the ventilators capacity of supplying high rates, etc.

The recruitment phase can suitably last from 10–100 seconds. With the ventilator according to the invention, the recruitment phase can be sustained for a longer period than in the prior art, since the superimposed breaths do cause some gas exchange.

DESCRIPTION OF THE DRAWINGS

Figure 1:
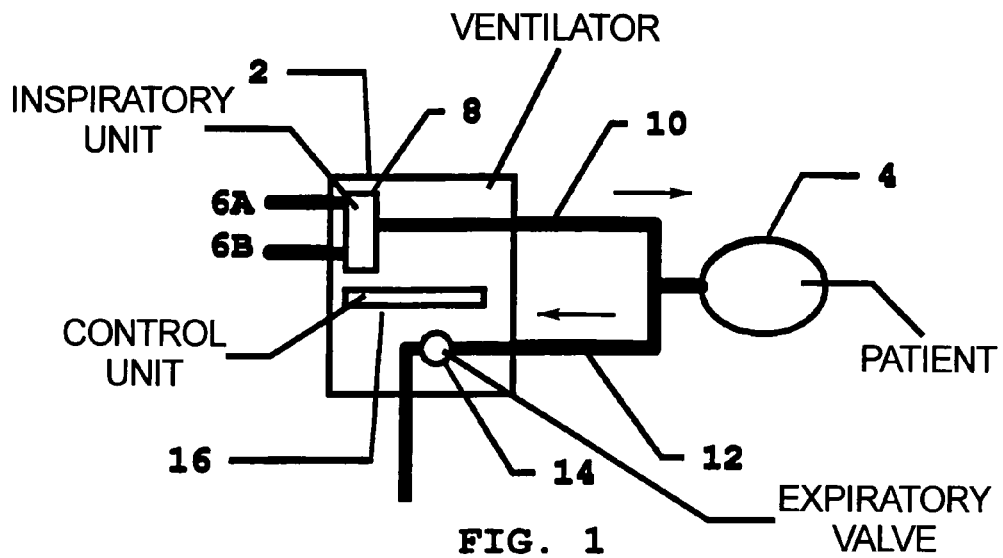
FIG. 1 shows one embodiment of a ventilator according to the invention.

FIG. 1 shows a ventilator 2 according to the invention. The ventilator 2 is connectable to a patient 4 in order to supply and evacuate breathing gases.

Breathing gas is delivered to the ventilator 2 through a first connector 6A and a second connector 6B, and an inspiratory unit 8 mixes the gases in the right proportion and with the right pressure and flow.

The breathing gas is then carried to the patient 4 in an inspiratory line 10 and from the patient 4 back to the ventilator 2 in an expiratory line 12.

An expiratory valve 14 then regulates the outflow of breathing gas from the ventilator 2.

The inspiratory unit 8 and expiratory valve 14 are controlled by a control unit 16 in order to generate the pressure and flows to which the patient 4 is to be subjected.

Figure 2:
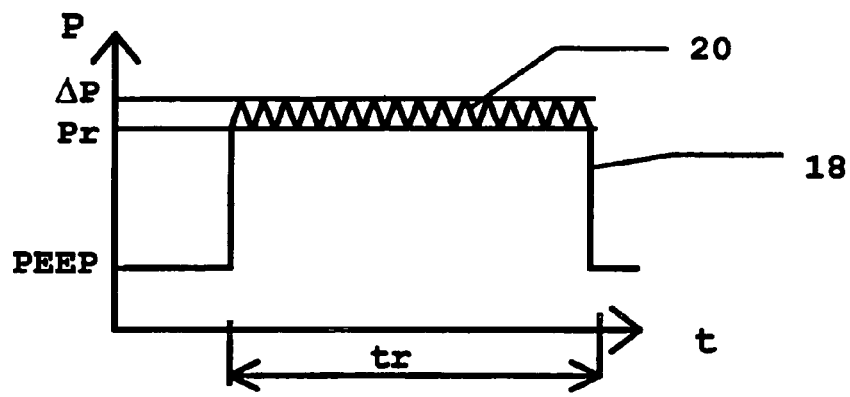
FIG. 2 shows a first example of a recruitment phase according to the invention.

Supplying the patient 4 with e.g. recruitment phases is possible. One example of such a phase is shown in FIG. 2. The recruitment phase is shown with a curve 18 in a pressure-time (P-t) diagram. In the recruitment phase, pressure from the basic pressure (PEEP), which can range from 0 to a positive pressure of 10–15 cmH$_2$O (or higher if the situation calls for it), is raised to an elevated basic pressure Pr. The elevated pressure Pr can be up to 80 cmH$_2$O. Breaths 20 are then superimposed on this basic pressure Pr. The breaths 20 are pressure-regulated and have a pressure amplitude ΔP from 1 to 10 cmH$_2$O. The superimposed breaths 20 are also imposed at a faster rate, i.e. from 50 to 200 breaths/minute.

The recruitment phase 18 has a duration tr lasting 10 to 100 seconds.

The objective of the recruitment phase is to open regions of the lung containing collapsed alveoli.

Figure 3:
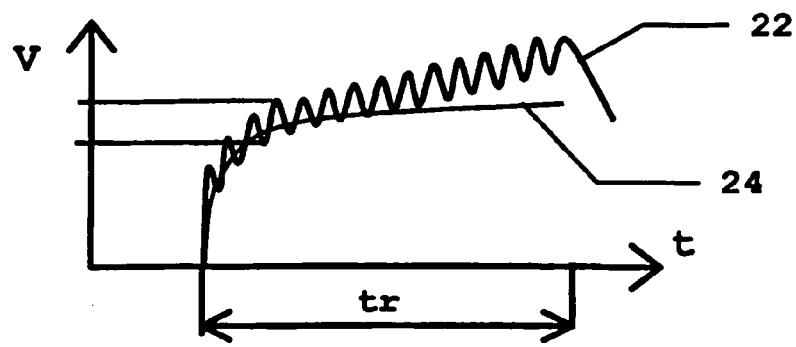
FIG. 3 shows a second example of a recruitment phase according to the invention.

FIG. 3 shows an alternative version of the recruitment phase. It depicts a volume-time (V-t) curve 22. As in the preceding example, an elevated basic pressure is imposed. In normal instances, this would generate an effect similar to the curve 24, but the curve 22 is instead achieved because of superimposed volume-controlled breaths. These breaths have a tidal volume of 1 to 100 ml.

As the FIG. 3 shows, the curve 22 ends with a larger total volume than the curve 24 at the end of the recruitment phase. This is because the superimposed breaths assist in opening more alveoli.

Although modifications and changes may be suggested by those skilled in the art, it is the intention of the inventor to embody within the patent warranted hereon all changes and modifications as reasonably and properly come within the scope of his contributions to the art.

I claim:

1. A ventilator comprising:
   an inspiratory unit;
   an expiratory valve;
   a control unit for controlling said inspiratory unit and said expiratory valve to regulate a flow of breathing gas by generating a recruitment phase with an elevated basic pressure for said breathing gas, with a plurality of breaths superimposed on said elevated basic pressure and an increased breathing rate with no withdrawal of said breathing gas.

2. A ventilator as claimed in claim 1 wherein said control unit controls said inspiratory unit and said expiratory valve to produce said elevated basic pressure in a range from 10 to 80 cmH$_2$O.

3. A ventilator as claimed in claim 1 wherein said control unit controls said inspiratory unit and said expiratory valve to generate said superimposed breaths at a pressure in a range from 1 to 10 cmH$_2$O.

4. A ventilator as claimed in claim 1 wherein said control unit controls said inspiratory unit and said expiratory valve to generate said increased breathing rate in a range from 50 to 200 breaths/minute.

5. A ventilator as claimed in claim 1 wherein said control unit controls said inspiratory unit and said expiratory valve to set said increased breathing rate as a percentage of a predetermined normal breathing rate.

6. A ventilator as claimed in claim 5 wherein said control unit sets said percentage to a percentage in a range between 110% and 1000%.

7. A ventilator as claimed in claim 1 wherein said control unit controls said inspiratory unit and said expiratory valve to generate said recruitment phase for a duration in a range between 100 to 100 seconds.

* * * * *